US008558705B2

(12) United States Patent
Gong et al.

(10) Patent No.: US 8,558,705 B2
(45) Date of Patent: Oct. 15, 2013

(54) CERAMIC SENSORS FOR WIRELESS SENSING

(75) Inventors: Xun Gong, Oviedo, FL (US); Linan An, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 557 days.

(21) Appl. No.: 12/821,993

(22) Filed: Jun. 23, 2010

(65) Prior Publication Data

US 2010/0321191 A1    Dec. 23, 2010

Related U.S. Application Data

(60) Provisional application No. 61/219,437, filed on Jun. 23, 2009.

(51) Int. Cl.
*G08B 17/00* (2006.01)
(52) U.S. Cl.
USPC .............. 340/584; 29/595; 340/626; 340/945
(58) Field of Classification Search
USPC .......... 340/584, 626, 540, 572.1, 572.7, 10.1, 340/693.5, 945; 29/595
See application file for complete search history.

(56) References Cited

U.S. PATENT DOCUMENTS

| | | | |
|---|---|---|---|
| 7,338,202 B1 * | 3/2008 | Kapat et al. ..................... | 374/10 |
| 2007/0074579 A1 * | 4/2007 | Cook et al. ..................... | 73/718 |
| 2008/0252401 A1 | 10/2008 | Margomenos et al. | |

* cited by examiner

*Primary Examiner* — Thomas Mullen
(74) *Attorney, Agent, or Firm* — Jetter & Associates, P.A.

(57) ABSTRACT

A RF resonator for sensing a physical or an environmental parameter includes a substrate having a substrate surface. A polymer-derived ceramic (PDC) element is positioned on or within the substrate surface. The RF resonator has a resonant frequency that changes as a function of the physical or environmental parameter. A system for wirelessly sensing at least one physical or environmental parameter includes at least one RF resonator and a wireless RF reader located remotely from the RF resonator for transmitting a wide-band RF interrogation signal that excites the RF resonator. The wireless RF reader detects a sensing signal retransmitted by the RF resonator and includes a processor for determining the physical or environmental parameter at the location of the RF resonator from the sensing signal.

27 Claims, 7 Drawing Sheets

CERAMIC SENSORS FOR WIRELESS SENSING

CROSS REFERENCE TO RELATED APPLICATIONS

This application and the subject matter disclosed herein claims the benefit of Provisional Application Ser. No. 61/219,437 entitled "WIRELESS CERAMIC SENSORS FOR HIGH-TEMPERATURE SENSING", filed Jun. 23, 2009, which is herein incorporated by reference in its entirety.

STATEMENT REGARDING FEDERALLY SPONSORED RESEARCH

This invention was made with Government support under Agency contract (NSF) ECCS-0823950 and NSF DMR-0706526 awarded by the National Science Foundation. The Government has certain rights in this invention.

FIELD

Embodiments of the invention are related to wireless sensors and wireless sensing systems therefrom.

BACKGROUND

Turbine engines currently play a dominant role in systems including power generation and aircraft propulsion. Current turbine designs have been limited by the lack of sensors capable of reliably providing detailed physical and chemical data in high-temperature (e.g., >1,000° C.) sections of such systems. For example, to further improve the performance and reliability and to reduce the pollution of turbine engines, robust sensors and sensor networks are needed for next-generation turbine technology to enable (i) obtaining detailed thermo-mechanical data to refine engine designs, (ii) providing online, real-time monitoring, and (iii) providing intelligent controls to make the engines "smart".

Currently, several technologies are under development for measuring the physical and chemical parameters within turbine engines. Optical-based non-contact technology is known for determining these parameters. However, optical-based non-contact technology has been shown to lack the necessary measurement accuracy and typically breaks down over time. Another technique measures these parameters without disturbing the work environment comprises using miniature sensors. Silicon carbide (SiC) and silicon nitride ($Si_3N_4$)-based ceramic microsensors have been investigated for high temperature and harsh environment applications. However, these sensors are restricted by limited fabrication methods, high cost, and a limited operation temperature range (typically <800° C.).

Polymer-derived ceramic (PDC)-based sensors and sensing systems using such materials are also known. PDC materials are generally formed by the processing of materials referred to as "preceramic polymers". Preceramic polymers are conventionally defined as polymers whose backbone contains C and at least one eteroatom (usually Si) that provides a ceramic residue (the PDC) through the elimination of organic moieties (by breaking of C—H bonds, and release of $H_2$ and $CH_4$ and other volatile compounds). The term "eteroatom" is used to indicate any atom of a cyclic molecule or of a cyclic portion of a molecule or ion, that is not carbon. The polymer-to-ceramic conversion is achieved either thermally (pyrolysis) or non-thermally (for instance by irradiation with ions), usually processing in controlled atmosphere. Polysiloxanes, polycarbosilanes, polysilanes and polysilazanes are some of the preceramic polymers currently available commercially, and they allow production of $SiO_2$, SiOC, SiC, $Si_3N_4$ and SiCN ceramics.

In one disclosed system for measuring the temperature or strain in an aircraft, PDC-based sensors are wired to a signal processing system. This system senses a resistance change due to the temperature/strain change experienced by the sensors. A limitation of the wired sensing arrangement is that they cannot be used for measurements in difficult to reach locations, such as important sections in turbine engines such as the turbine blades, and sections that are blocked by the turbine blades. There is thus a need for new high temperature (e.g., >1000° C.) capable sensors and sensing systems that can sense parameters in any section of a turbine engine or in other space-limited high-temperature and harsh environment applications.

SUMMARY

Embodiments of the invention include passive RF resonators and systems therefrom for wirelessly sensing at least one physical or environmental parameter. The RF resonator includes at least one PDC element and the system adds a wireless RF reader. Since the wireless RF reader can be spaced apart from the RF resonator, for high temperature applications the wireless RF reader can be positioned outside the high temperature region.

The PDC elements possess complex nano-structures in which nano-crystalline phases (such as SiC or $Si_3N_4$), unique amorphous phases (e.g., SiOC or SiCN) and a free carbon phase (i.e. turbostratic carbon in which C atoms are not directly bonded to Si atoms), co-exist. PDCs are known to provide low creep rate, high chemical resistance and a higher thermal stability in comparison to conventional ceramics such as SiC and $Si_3N_4$. As defined herein, a PDC is a ceramic that includes amorphous phases and a free carbon phase (i.e. turbostratic carbon in which C atoms are not, directly bonded to Si atoms), and also includes at least one heteroatom, and resists thermal decomposition and large-scale crystallization up to at least 1,000° C., and generally up to at least 1,200° C. Some PDCs provide resistance to thermal decomposition and large-scale crystallization up to about 1,800° C. As defined herein, a PDC is a ceramic that includes amorphous phases and a free carbon phase (i.e. turbostratic carbon in which C atoms are not directly bonded to Si atoms), includes at least one heteroatom, and resists thermal decomposition and large-scale crystallization up to at least 1,000° C., and generally up to at least 1,200° C.

Disclosed RF resonators and systems are thus high-temperature tolerant (generally at least 1,000° C.) and provide online, real-time monitoring for applications such as in turbine engine systems where survival under extremely harsh conditions (e.g., >1000° C. and/or a corrosive atmosphere) is needed.

Being wireless, such systems also allow sensing in otherwise difficult to reach system locations, including generally any section of a turbine engine, including around the turbine blades. Moreover, the RF resonators according to embodiments of the invention generally provide Q-factors ≥100 which enable more accurate and long-range wireless sensing. As used herein, RF is defined as electromagnetic radiation that has a wavelength ranging from hundreds of meters to about one millimeter.

The RF resonator generally comprises a substrate having a substrate surface and at least one PDC element positioned on or within the substrate surface. The RF resonator has a resonant frequency that changes as a function of the physical or environmental parameter to be sensed by the system. The RF resonator is generally a MEMS-based resonator.

In the system embodiment, the wireless RF reader is located remotely from the RF resonator, and is generally in a room temperature or a near-room temperature location. The RF reader transmits an RF interrogation signal that is generally a wideband RF signal that includes the resonant frequency of the RF resonator to excite the RF resonator, which retransmits a sensing signal in response. As used herein, a "wideband signal" is a signal that covers a frequency spectrum ≥5% fractional bandwidth, where the fractional bandwidth is the ratio of a signal's actual bandwidth to its center frequency. The RF reader detects the sensing signal from the resonator and includes a signal processor for processing the sensing signal to determine the physical or environmental parameter at the location of the sensor, such as temperature or pressure. The RF reader generally includes a non-volatile memory that stores a calibration relation that enables obtaining the parameter of interest from the frequency information contained in the sensing signal. The calibration data can be in table form, such as a relation between temperature/pressure and the resonant frequency.

BRIEF DESCRIPTION OF THE DRAWINGS

FIGS. 2A-C show different geometries for evanescent-mode resonators for pressure sensing, while FIG. 2D shows a simplified cross section depiction of an exemplary evanescent-mode resonator for pressure sensing, according to embodiments of the invention.

DETAILED DESCRIPTION

Figure 1:
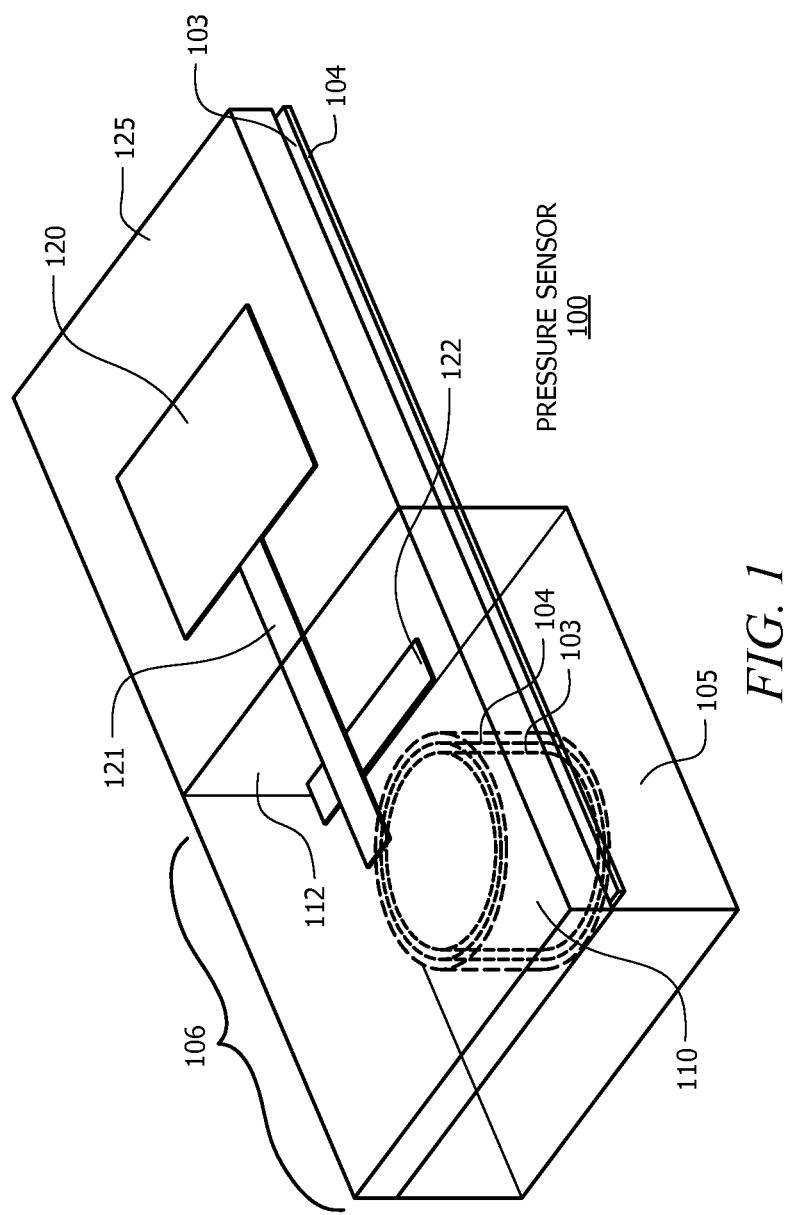
FIG. 1 shows the structure of an exemplary evanescent-mode resonator pressure sensor including a coupling structure, according to an embodiment of the invention.

Disclosed embodiments in this Disclosure are described with reference to the attached figures, wherein like reference numerals are used throughout the figures to designate similar or equivalent elements. The figures are not drawn to scale and they are provided merely to illustrate the disclosed embodiments. Several aspects are described below with reference to example applications for illustration. It should be understood that numerous specific details, relationships, and methods are set forth to provide a full understanding of the disclosed embodiments. One having ordinary skill in the relevant art, however, will readily recognize that the subject matter disclosed herein can be practiced without one or more of the specific details or with other methods. In other instances, well-known structures or operations are not shown in detail to avoid obscuring structures or operations that are not well-known. This Disclosure is not limited by the illustrated ordering of acts or events, as some acts may occur in different orders and/or concurrently with other acts or events. Furthermore, not all illustrated acts or events are required to implement a methodology in accordance with this Disclosure.

Notwithstanding that the numerical ranges and parameters setting forth the broad scope of this Disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

One embodiment of the invention comprises an evanescent-mode resonator pressure sensor. The structure of an exemplary evanescent-mode resonator-based pressure sensor 100 including a coupling structure according to an embodiment of the invention is shown in FIG. 1. Pressure sensor 100 comprises an evanescent-mode resonator 106 that comprises a substrate 105 and a cavity 112 formed within the substrate 105, and at least one PDC element 110 generally referred to herein as a PDC post 110 within the cavity 112. The PDC elements can be in a variety of shapes other than the round cross sectional shape shown, such as a square or rectangular cross section. Top plate 125 encloses the cavity 112. Top plate 125 is thin enough to be flexible to function as a membrane that flexes under pressure. For example, an exemplary thickness range for top plate 125 is 50-200 μm. In one embodiment the top plate comprises a PDC, such as SiAlCN, SiCN, or SiBCN.

As known in the art, PDCs possess a set of high-temperature thermo-mechanical properties that the Inventors have recognized make them suitable for applications in gas turbine and other hostile (e.g., high temperature and corrosive atmosphere) environments. As noted above, PDCs are thermally stable and resist large-scale crystallization at temperatures of at least 1,000° C. and their creep resistance exceeds that of conventionally used polycrystalline SiC and $Si_3N_4$. The Inventors have demonstrated that PDCs such as SiAlCN exhibit an anomalously high resistance to oxidation and hot-corrosion, which is a major limit for conventional SiC and $Si_3N_4$-based sensors that are currently under investigation for high-temperature applications.

The inventors have also recognized that PDCs have excellent microfabrication capability and compatibility with existing silicon-based microfabrication (e.g., MEMS) processing. Unlike conventional ceramic materials (e.g., SiC and $Si_3N_4$), PDC-based micro-devices can be fabricated using well-developed semiconductor processing technologies, generally including photolithography and deep reactive-ion etching (DRIE). DRIE can be used to form deep cavities disclosed herein. As disclosed herein, the thin or thick film micro-devices can be first fabricated in organic (preceramic) form and then be converted to PDCs by pyrolysis. Recently, microfabrication techniques such as micro-casting, lithography and polymer-based bonding have been developed, which may also be used.

PDCs can also be formed by processing organic thin/thick film precursors using spin-on coating methods and patterned into desired thin film or thick film devices. In this process, the precursor for PDCs, which is either a liquid or dissolvable into an organic solvent, can be modified to be photosensitive and processed similar to photoresist and patterned using conventional photolithography.

Significant to temperature sensing embodiments of the invention, the Inventors have recognized that PDCs possess unique temperature-dependent dielectric properties. A property of PDCs such as SiCN is that the electrical conductivity of PDCs can be varied across a large range by tailoring the composition of the materials, from insulator (dielectric) to semiconductor. When in the insulator state, the Inventors have recognized that PDCs possess a dielectric constant that increases monotonically with temperature. This change in dielectric constant, which can be used to monitor temperature according to an embodiment of the invention, is much more significant than that for other high-temperature materials, such as $Al_2O_3$, and thus provides higher measurement sensitivity. Furthermore, the dielectric constant of the PDC element can also be tuned by varying the initial polymer composition to meet different requirements for interfacing with a wireless sensor in a disclosed sensing system.

The PDC post 110 can comprise a semiconductor or a dielectric. The size of the cavity 112, the size of the PDC post 110, and the gap between the PDC post 110 and the walls of the cavity 112 including the top plate 125 sets the nominal resonant frequency and the Q factor of the resonator 106. As used herein, the "nominal resonant frequency" means the resonant frequency at standard temperature and pressure conditions (25° C. and 1 atmosphere pressure). The resonator 106 generally provides a nominal resonant frequency between 1 and 40 GHz and a Q value ≥100. The PDC post 110 is shown including a metal coating 103 and a dielectric coating 104 on the metal coating 103 that prevents oxidation (and corrosion) of the metal.

Metal coating 103 can comprise a refractory metal that has a melting point >1500° C., such as tungsten (W), tantalum (Ta) platinum (Pt) or titanium (Ti), or related compounds such as WN, TaN or TiN. Top plate 125 is also shown including a metal coating 103 and a dielectric coating 104 on the metal coating. Although not shown, the walls of the cavity 112 can also include a metal coating 103 and a dielectric coating 104 on the metal coating. When the metal coating 103 is non-oxidizable under the conditions for a given application, the dielectric coating 104 is not needed. It is possible for the PDC post 110 to be replaced by a post formed entirely of a high-temperature metal.

RF resonators according to embodiments of the invention having high-Q factors generally enable electromagnetic energy from an interrogation signal received to be stored for a longer time (as compared to lower Q-factor resonators) within the RF resonator before being retransmitted as a sensing signal back to the reader. The reader therefore is able to receive a stronger sensing signal from the RF resonator due to the high-Q, and perform signal processing on the stronger signal which enables more accurate and longer-range wireless sensing as compared to known related sensing systems.

The loading by the PDC post 110 lowers the resonant frequency of the cavity 112 and thus the resonator 106, which allows an RF signal of a certain frequency to resonate within an otherwise much smaller cavity to provide a relatively small structure for lower frequency operation. The resonant frequency of resonator 106 is generally based on the size of the cavity 112, the size of the PDC post 110, and the gap (distance) between the cavity 112 and the PDC post 110. The resonant frequency of the resonator 106 changes based on deflection of the top plate 125 which changes the gap and thus the pressure (based on calibration relation) in the vicinity of the resonator 106 that can be sensed by a wireless RF reader (not shown in FIG. 1). Pressure sensor 100 is also shown including a coupling structure comprising antenna 120 shown as a planar antenna and microstrip line 121 both shown on the top plate 125. Analogous to metal coating 103, antenna 120 and microstrip line 121 can comprise a refractory metal that has a melting point >1500° C., such as W, Ta, Pt, Ti, or related compounds such as WN, TaN or TiN. The slot 122 formed in top plate 125 shown in FIG. 1 couples RF energy into and out from the resonator 106.

The PDC post 110 is generally metallized (as is the inside surface of the cavity 112) before the bonding the top plate 125 to enclose the cavity 112. In operation, air or the gas environment in the application fills the cavity 112.

For pressure sensor 100, the minimum achievable gap dimension is generally limited by the fabrication tolerances of the PDC post 110 or other feature microfabrication. Once this minimum gap dimension is determined, the dimensions for cavity 112 and the PDC post 110 can generally be set to achieve maximum size reduction and sensitivity. The antenna 120 is generally a planar antenna to minimize size, such as a patch antenna, which can be designed around the center frequency of the resonator 106 for coupling RF energy between the pressure sensor 100 and a reader unit (not shown). As known in the art, the coupling between microstrip line 121 and slot 122 can be designed to achieve maximum electromagnetic energy coupling to and from the resonator 106.

Figure 2:
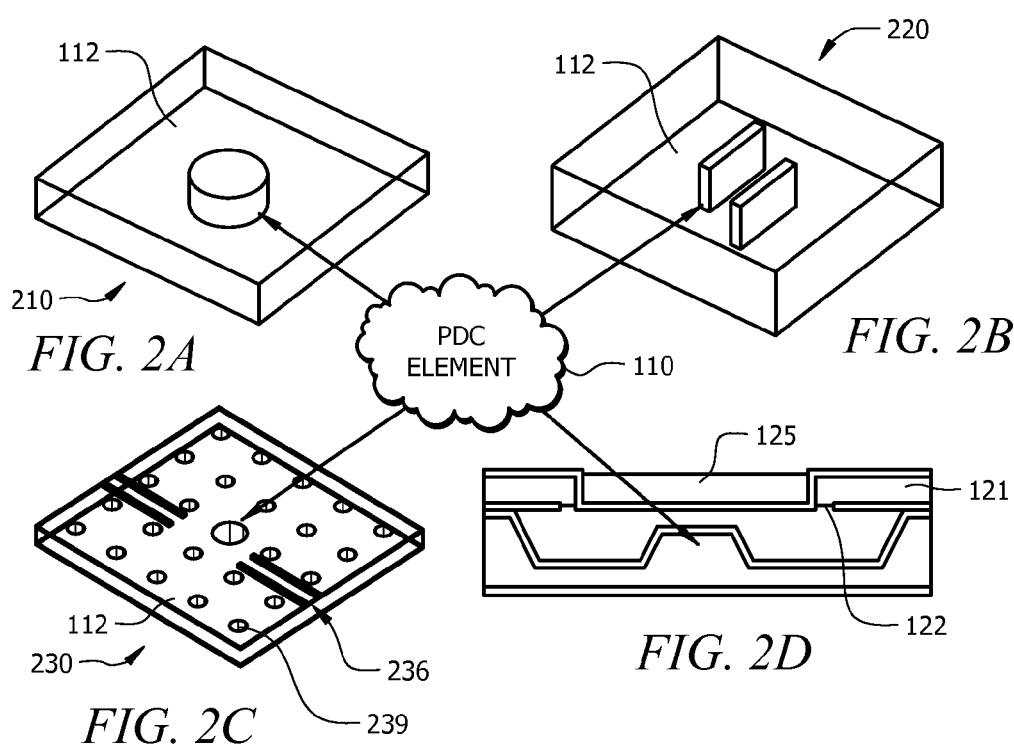

Evanescent-mode resonators for pressure sensing showing several different exemplary PDC feature geometries are illustrated in FIGS. 2A-C, with a cross section depiction of an exemplary resonator shown in FIG. 2D. As described above, the resonant frequency of the evanescent-mode resonator is sensitive to the pressure change around the sensor based on flexure of the top plate 125, such as the pressure inside an engine chamber.

Resonator 210 shown in FIG. 2A has a load comprising a single cylindrical PDC element 110 shown as a PDC post that is within the cavity 112. Resonator 220 shown in FIG. 2B has a pair of vertical parallel PDC plates 110 in the cavity 112. Resonator 230 shown in FIG. 2C has a center cylindrical PDC post 110 in cavity 112 along with a periodic array of vias. The coplanar waveguide (CPW) feeds 236 shown are for coupling RF energy into the cavity. The function of the vias 239 shown is to form a boundary to help confine the RF energy inside the cavity 112. FIG. 2D shows a simplified cross section depiction of an exemplary resonator showing another shaped PDC post 110 and a top plate 125 including a slot 122 and a microstrip feed line 121.

As noted above, by loading the cavity 112 with one or more PDC posts 110, the resonant frequency of the resonator 106 can be reduced, while a relatively high unloaded Q factor is still maintained. The size reduction of the cavity 112 can be up to one order of magnitude as compared to known structures, depending on the height of the PDC post 110 relative to the height of the cavity 112. However, sensitivity analysis that was performed by the Inventors (See FIG. 4 described below) has demonstrated that fabrication tolerances become sensitive when the PDC post height is close to the cavity height (i.e. close to the top plate 125), representing a high loading factor.

Precision manufacturing techniques such as layer-by-layer polymer stereolithography processing can be used to realize capacitively loaded cavities in different geometries. The small fabrication tolerances enable the accurate prediction of the desired post (or feature) heights, and in turn, achieve the desired resonant frequencies. As described above, the resonant frequency is significantly reduced due to the increased capacitance caused by the small gap between the top of the PDC post 110 and the top plate 125 of the cavity 112. However, the metal loss which is associated with the tangential magnetic field on the metal surfaces does not change significantly. Loading a cavity with a post does not change the magnetic field distribution significantly. Since the metal loss does not degrade significantly, the resulting unloaded Q factor of the resonator 106 is not degraded significantly.

A quasi-static analysis can be used to derive the relationship between the height of the PDC post 110 and resonant frequency of the cavity 112. An equivalent circuit model was developed to match Eigen value solutions obtained using Ansoft High Frequency Structure Simulator (HFSS) full-wave analysis (Ansoft Corporation, Pittsburgh, Pa.). The total capacitance of the resonator shown in FIG. 2A is given by:

$$C_{Total} = C_{Post} + C_{Remaining}, \quad (1)$$

where $C_{Remaining}$ is the remaining capacitance between the top and bottom plates of the cavity 112 excluding the area occupied by the PDC post 110. The PDC post's area adds a capacitance value $C_{post}$ that can be approximated by idealized quasi-static formula for a parallel plate capacitor, where d is the distance between the top of the dielectric post 110 and the top plate 125 of the cavity 112.

$$C_{post} = \frac{\varepsilon_r \varepsilon_0 A}{d}. \quad (2)$$

The resonant frequency of the resonator 106 can be approximated by:

$$\omega \approx \frac{1}{\sqrt{L(C_{post} + C_{remaining})}} \quad (3)$$

Understanding the sensitivity of the resonant frequency to fabrication tolerances allows realization of highly loaded evanescent-mode resonators for pressure sensing according to embodiments of the invention. For given fabrication tolerances and filter specifications, the achievable percentage of loading can be determined from a sensitivity analysis. Though the resonant frequency may be as low as desired by reducing the gap (d) between the PDC post 110 and top plate 125 of the cavity 112, repeatability can become an issue as the gap is reduced and the capacitance increases.

Figure 3:
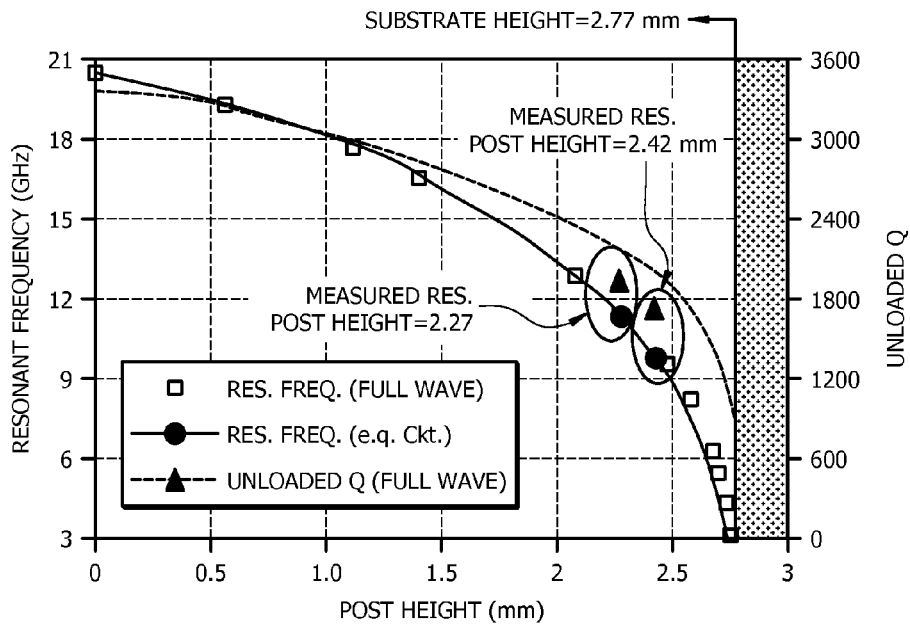
FIG. 3 shows frequency and Q-factor changes versus the post height for a cavity size 10.35 mm×10.35 mm×2.77 mm and a post diameter 3.248 mm, according to an embodiment of the invention.
Figure 4:
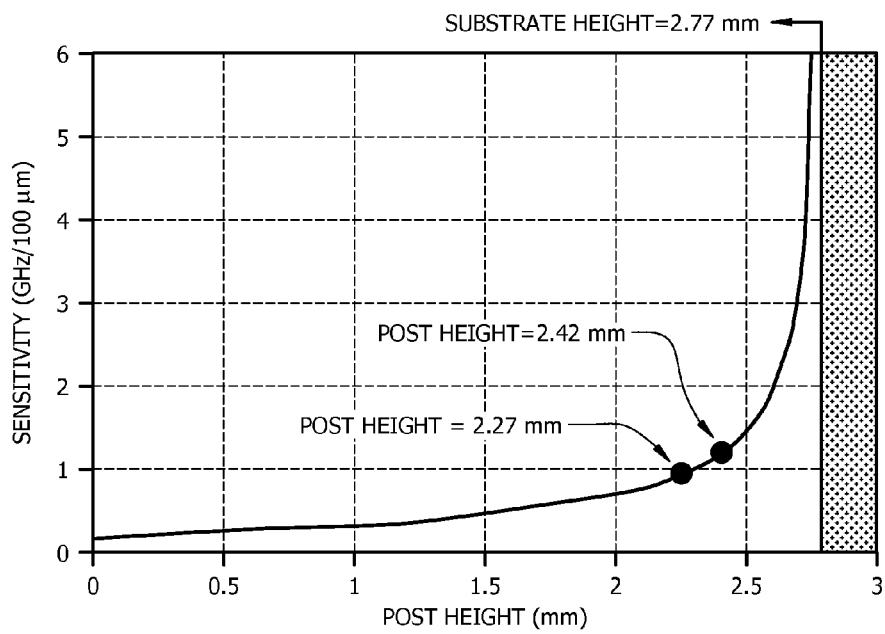
FIG. 4 shows a sensitivity analysis for an evanescent-mode resonator for pressure sensing, according to an embodiment of the invention.

The frequency and Q factor changes versus the post height for an example evanescent-mode resonator comprising a cavity size of 10.35 mm×10.35 mm×2.77 mm and a PDC post 110 diameter of 3.248 mm are shown in FIG. 3. As the height of the PDC post 110 approaches the height (2.77 mm) of the cavity 112, as shown in FIG. 3, the resonant frequency for the resonator is seen to decrease. The sensitivity analysis for this evanescent-mode resonator is shown in FIG. 4 showing an increased sensitivity as the post height approaches the substrate height.

During operation of the evanescent-mode resonator, when the air (or other gaseous environment) pressure changes, the membrane (top plate 125 of the cavity 112) above the dielectric post 110 adapts to a different degree which changes the gap that creates a capacitance change. Therefore, the resonant frequency of the resonator changes as a function of air pressure. The distributed nature of the evanescent-mode resonator generates a very high unloaded Q factor (≥100, such as >1,000) as compared to conventional Q factors of 6 for known resonators. This high unloaded Q factor facilitates wireless sensing as described below. Moreover, the working frequency of disclosed evanescent-mode pressure sensors is generally in low GHz region, such as 1 to 15 GHz in one embodiment. As a result of low GHz operation, the antenna size can be much smaller as compared to the antenna size for conventional operation in the tens of MHz and is thus more practical to realize inside small spaces such as engine chambers.

Figure 5:
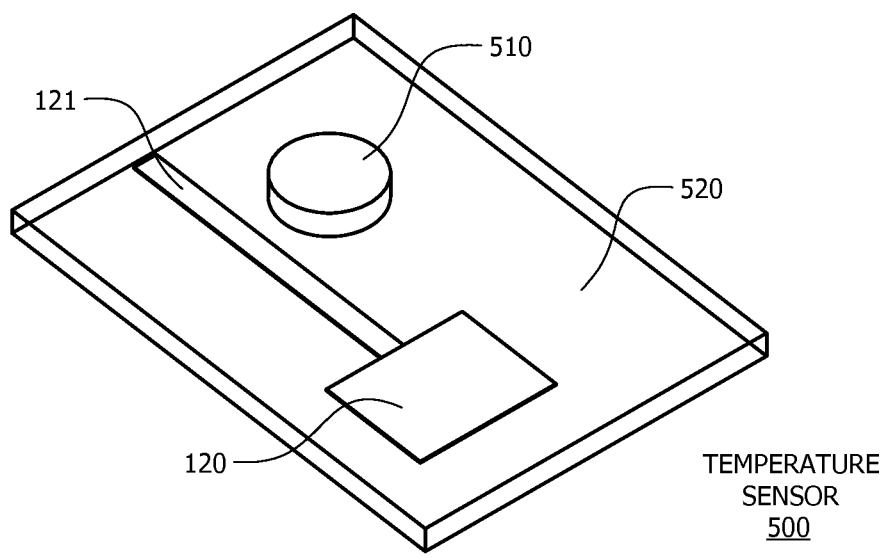
FIG. 5 shows the structure of an exemplary PDC dielectric resonator (DR)-based temperature sensor, according to an embodiment of the invention.

In another embodiment the sensor system comprises a temperature sensing system wherein the PDC resonant element comprises a dielectric PDC having a temperature dependent dielectric constant positioned on a surface of a substrate. Unlike the pressure sensor embodiment described above, there is no multi-element capacitor structures formed. The structure of a PDC dielectric resonator (DR)-based temperature sensor 500 according to an embodiment of the invention is illustrated in FIG. 5. At least one DR 510 is generally formed on a ceramic (e.g., PDC) substrate 520. The DR 510 has a distributed L, R and C and thus alone functions as a high Q resonator. An antenna 120 such as the patch antenna described above can be designed around the center frequency of the DR 510. A microstrip line 121 is used to couple RF energy into and out from the DR 510 by proximity. The distance between the DR 510 and the microstrip line 121 can be set to achieve a desired amount of coupling.

The resonant frequency of the DR 510 is generally determined by its shape, size, and dielectric constant. The nominal resonant frequency of the DR 510 is generally between 1 and 40 GHz, and DR 510 generally provides a Q value ≥100. Although the shape of DR 510 shown in FIG. 5 is cylindrical, the DR 510 can be provided in a variety of other shapes. In operation, the temperature-dependent dielectric constant of the PDC changes the resonant frequency of the DR 510, and given a calibration relation the temperature can be determined from the frequency content of the retransmitted signal from the DR 510.

The Inventors have designed a measurement setup to characterize the dielectric constant of PDCs at high temperatures and high frequencies. Using the characterization data, the measured dielectric constant can be used to design the resonant frequency of the ceramic temperature sensor.

DRs are known for use in high-Q factor resonators in the microwave and millimeter-wave regions. The Inventors have recognized that the use of a dielectric resonator fabricated from a low-loss material can produce very high Q-factors due to the high concentration of electromagnetic energy inside DRs and the absence of the conductor loss. Full-wave simulation shows that typically >90% of electric field is confined within the DR. This phenomenon can be observed from the electric field distribution of $HEE_{11}$ mode inside a DR. Therefore the resonant frequency of the ceramic MEMS temperature sensor is approximately proportional to $1/\sqrt{\in_r(T)}$, where $\in_r(T)$ is the temperature-dependent dielectric constant of SiCN. The unloaded Q of the DR is given by:

$$\frac{1}{Q_{Unloaded}} = V_{DR}\tan\delta_{DR} + V_{Sub}\tan\delta_{sub} + \frac{1}{Q_{metal}}. \quad (4)$$

Since most of the electric field is confined inside the DR 510, $V_{DR} \approx 1$ and $$\frac{1}{Q_{Unloaded}} \approx \tan \delta_{DR}.$$

The loss tangent of the PDCs can be reduced to its lowest value to realize high-Q factor dielectric resonators.

As described above, embodied as a temperature sensor, the temperature-dependent dielectric constant of the PDCs is generally utilized. The resonant frequency of the temperature sensor is proportional to $1/\sqrt{\in_r(T)}$, where $\in_r(T)$ is the temperature-dependent dielectric constant of the PDCs. The PDC-based high-Q factor resonators offer several unique advantages over conventional SiC or $Si_3N_4$ sensors such as ease of microfabrication and excellent corrosion resistance.

Figure 6A:
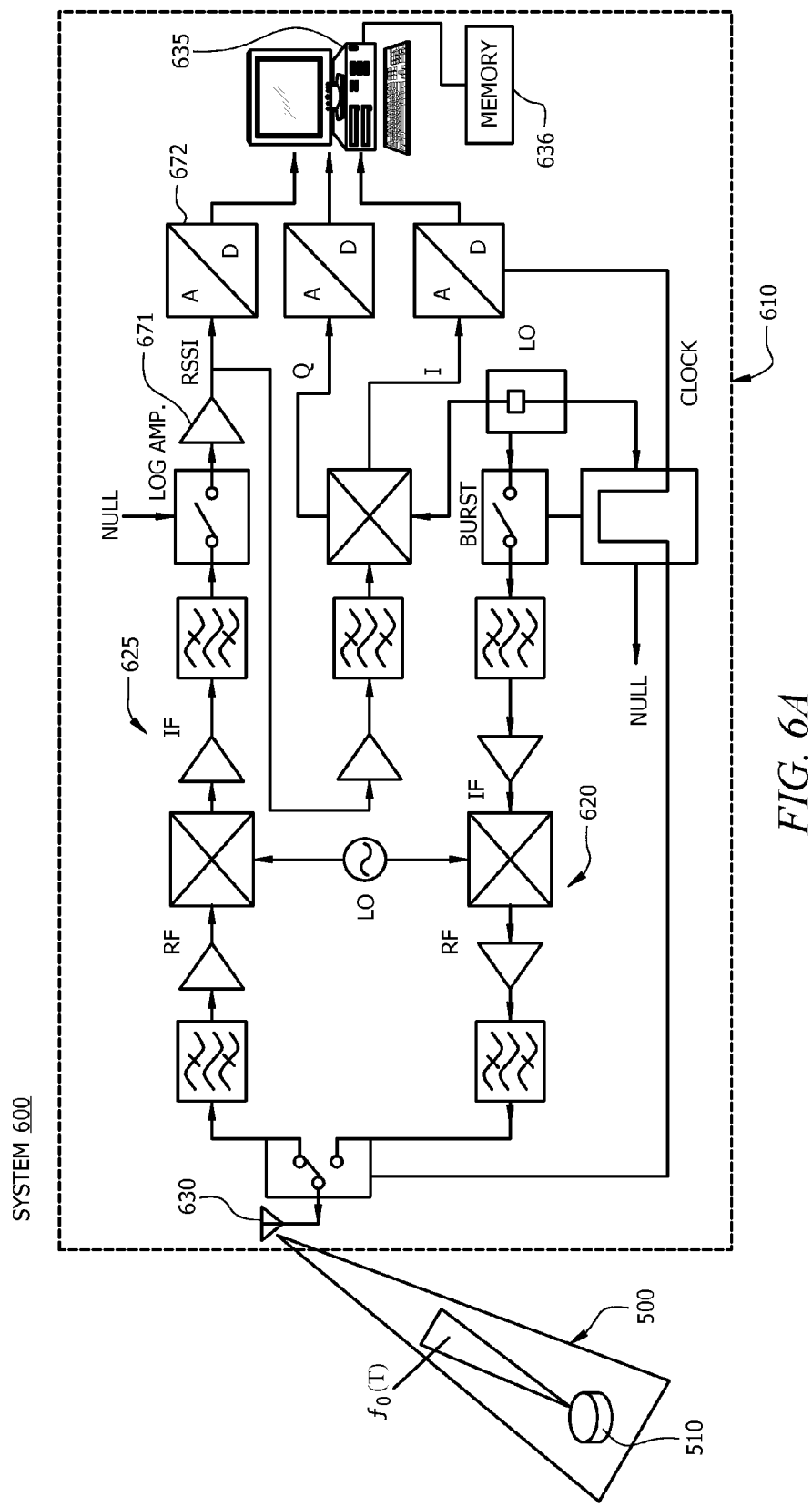
FIG. 6A is block diagram of wireless sensor system, according to an embodiment of the invention.

A block diagram of a sensor system 600 comprising a temperature sensor 500 and a wireless RF reader 610 according to an embodiment of the invention is illustrated in FIG. 6A. The temperature sensor 500 as described above is made of PDCs configured as a high-Q factor DR-based resonator 510 which has a resonant frequency $f_o$ that is a function of temperature ($f_o(T)$). This passive ceramic temperature sensor 500 can be miniature (e.g., ~1-10 mm) and can be mounted using high temperature tolerant bonding materials to adhere the sensor to the turbine on an engine blade or other high-temperature location (See FIG. 6C described below), in which DR 510 resonates at a unique resonant frequency depending on its geometry.

The RF reader unit 610 includes an RF signal transmitter section 620 and RF receive section 625 that is generally located in a room temperature, or near room temperature environment. RF signal transmitter section 620 transmits a wide-band RF signal via reader antenna 630 which is received by the DR 510 of temperature sensor 500. The wireless reader 610 detects the sensing signal retransmitted by the DR resonator 510 which is a function of the temperature, pressure or other parameter at the location of the sensor and processor 635 which is coupled to memory 636 processes the sensing signal.

In wireless passive sensing, a time delay between the echoes from the passive transponder and the environment is typically used to isolate the interference from nearby objects and increase sensing accuracy. In conventional SAW sensing systems, delay lines are frequently used for this purpose. However, long delay lines are very difficult to realize on non-piezoelectric substrates at high temperatures. An alternative is to use a resonator such as DR 510 which effectively achieves the necessary delay time.

Figure 6B:
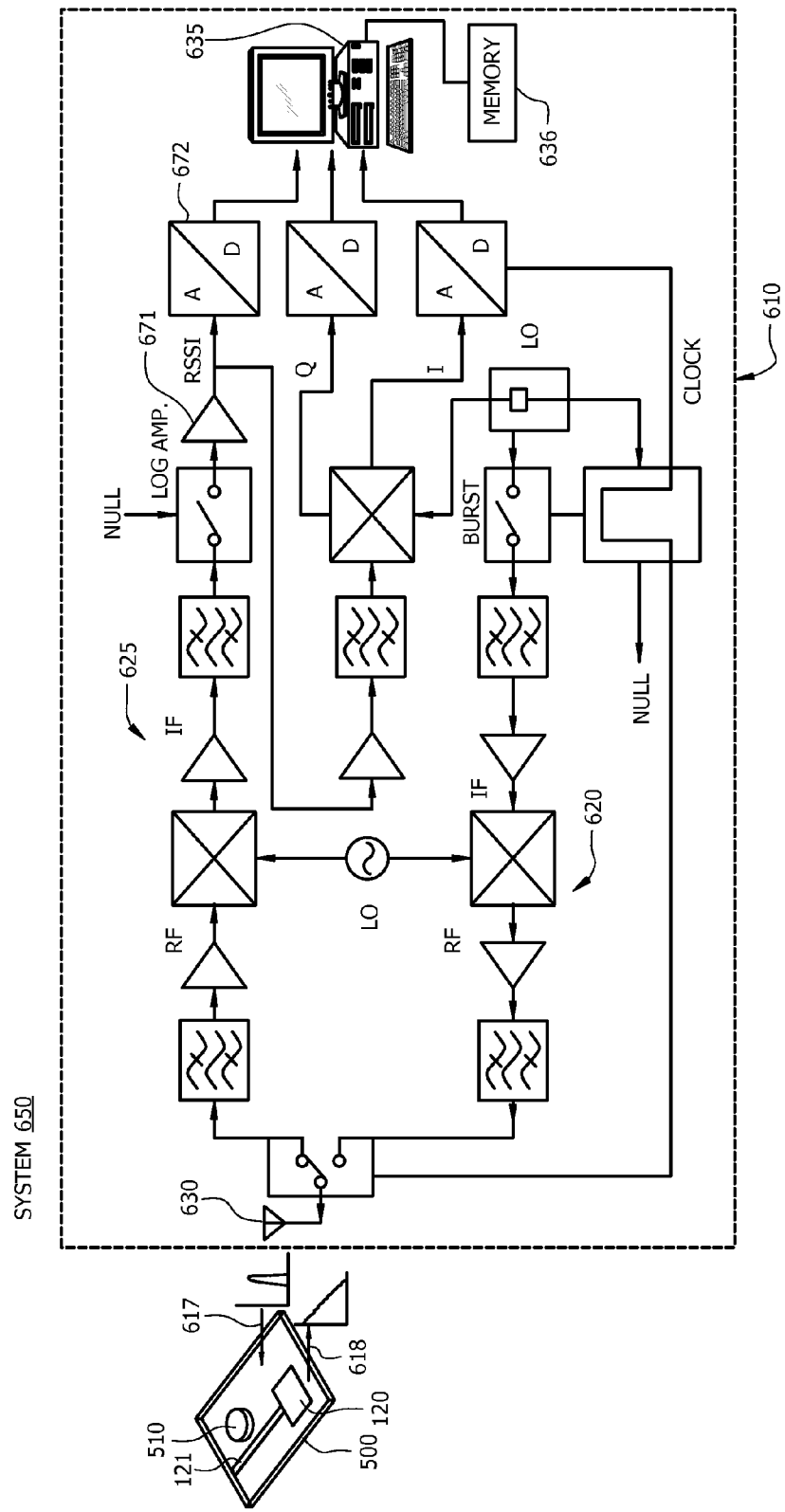
FIG. 6B is block diagram of wireless sensor system, according to another embodiment of the invention.

FIG. 6B shows the schematic layout of a sensor system 650 including a DR-based temperature sensor 500 and a wireless RF reader 610, according to an embodiment of the invention. An interrogation signal 617 shown as a RF request signal from the reader unit 610 excites the DR 510. The received energy is stored in the DR 510. The number of stored wavelengths is given by the quality factor Q, which also determines the decay time of the DR 510. This interrogation signal 617 is delayed and retransmitted as the RF response 618 shown by the temperature sensor 500 to the reader unit 610.

In order to substantially eliminate the interrogation signal and all environmental echoes (which can contribute noise), the sensing signal response of temperature sensor 500 can be gated in the time domain. After a subsequent Fourier transform, the resulting peaks in the frequency domain can be evaluated by the reader unit 610 to retrieve the sensor information. More sophisticated algorithms can be used instead of the Fourier transform to determine the resonant frequency of DR 510 with higher accuracy.

Figure 6C:
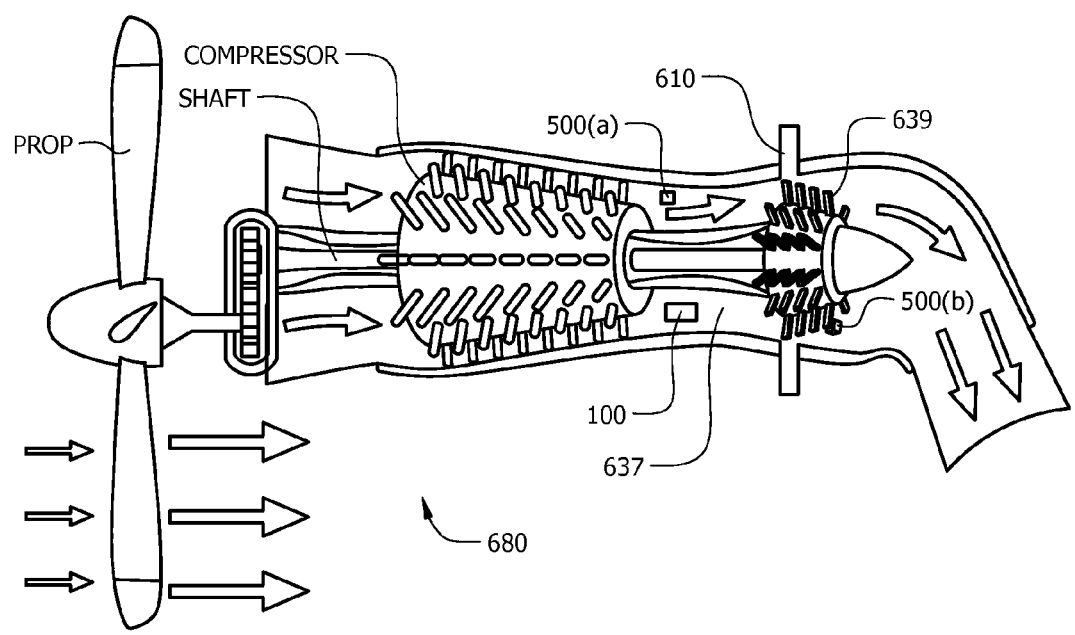
FIG. 6C is a depiction of a system showing a portion of a turbine generator including a plurality of temperature sensors and a pressure sensor mounted therein, along with a wireless reader, according to an embodiment of the invention.

FIG. 6C is a depiction showing a system section comprising a portion of a turbine generator 680 including a plurality of temperature sensors 500(a) and 500(b) and a pressure sensor 100 mounted therein using high temperature tolerant bonding materials to adhere the respective sensors therein including temperature sensor 500(b) on one of the engine blades 639 of the turbine generator 680, along with a wireless reader 610, according to an embodiment of the invention.

The wireless readers 610 for interrogation can be similar to those used in conventional radar applications. Particularly, reader unit 610 based on pulsed radars is generally able to achieve best performance values, operation over a broad frequency range, and a high degree of modularity. If there is at least one temperature sensor 500 within the detection range, it reflects a pulse train after a delay time of several microseconds. The incoming sensor pulses are first amplified then down-converted in the IF-band by the reader unit 610. The log amplifier 671 following the IF filter has one output for the amplitude and another with the limited signal for detecting the phase information.

A quadrature demodulation as shown is employed to get the in-phase and quadrature component out of the limited signal. After demodulation and digitizing the A/Ds 672 shown, the sensing signal is evaluated by a processor (e.g. microprocessor) 635 which is coupled to memory 636 for processing the sensing signal. Because the system operates fully coherent with respect to the local oscillator, many RF responses can be summed up to enhance the signal-to-noise ratio (SNR), thus leading to an improvement of the maximum read-out distance.

Although a single sensor is generally described herein, embodiments of the invention such as the turbine generator 680 shown in FIG. 6C include a plurality of sensors for multiple measurements from multiple locations within the system. Since the resonant frequency of each individual sensor can be tuned to be unique by tailoring its geometry as described above, a single reader unit can be used to detect multiple sensors simultaneously to address the need of temperature/pressure sensing at different sensing locations. Modulation techniques known in the art of communications can also be used to provide an identifier to each sensor in an array of sensors that have the same resonant frequency (e.g., time slots in a time multiplex).

Exemplary fabrication details will now be described.
Micro-Fabrication and Characterize High-Temperature Dielectric Properties of PDCs for Sensors As described above, it has been demonstrated PDCs can be microfabricated using several known techniques, such as micro-casting and lithography. Lithography-based techniques can be adapted for the fabrication of the sensors. Lithography-based fabrication has many advantages, including excellent patterning capability and dimensional accuracy. However, unlike well-developed photoresist, polymeric precursors that are used to synthesize PDCs generally exhibit poor photo-polymerization capability due to the lack of necessary functional groups, which in turn leads to some processing difficulties.

Processing difficulties include the need for (1) high-energy ultraviolet (UV) source and long exposure times to cure the precursors; and (2) the obtained patterns sometimes lack dimensional accuracy and uniformity. In one embodiment the photo-polymerization ability of the precursors are improved by modifying them with monomers containing vinyl groups. Such vinyl groups, can be added to the precursors through chemical reactions of the precursors and the monomers, and can be easily attacked by free radicals generated by UV exposure of the photo initiator to realize photo-polymerization. Results have indicated that this is an effective approach to improve the patterning capability of PDC thin and thick films.

The dielectric properties of various PDCs were characterized by the inventors up to 1200° C. The Inventors have demonstrated that the dielectric constant of PDCs generally increase with increasing temperature up to 1000° C. and the dielectric constant is expected to increase monotonically up to at least 1400° C.

Fabrication of Sensors

Regarding fabricating an evanescent-mode resonator-based pressure sensor, such as pressure sensor 100 shown in FIG. 1, an exemplary fabrication process for forming the pressure sensor is described below. The sensor base part and cavity cap (top plate) can be fabricated separately and then integrated together via diffusion bonding or another suitable bonding technique.

For fabricating the base part, the plate is generally made from PDC precursors which can be used as the substrate. The dielectric features such as posts in the cavity can be fabricated on the substrate using the lithographic techniques described above. The height of the PDC post or other feature can be accurately controlled by this fabrication generally to ~50 μm. The base material which is used to form the cavity can then be converted to a PDC by pyrolysis, and then coated with high-temperature tolerant metals (e.g., Pt, Pd), such as using a sputtering process to form a metal coating. As described above, a protective dielectric coating can be formed on the metal coating.

The cap (top plate) portion can be fabricated similarly. First, a thin film, such as having a thickness ranging from 50-200 μm can be fabricated from selected PDC precursors, and a holding ring, which is used to handle the sample, can be fabricated on the top of the film. The cap is then converted into a PDC by pyrolysis, and then metallized using the same metal and sputtering technique described above.

After their respective fabrications, the base and cap portions can be bonded together, such as using diffusion bonding between the metals. Since thermodynamic data for metals, such as Pt and Pd, is available, the conditions for diffusion bonding can be determined.

An exemplary procedure for fabricating a temperature sensor according to an embodiment of the invention is now described. First, a resonator including at least one resonator feature can be fabricated on a substrate made from PDC precursors. The PDC precursors can then be converted to a ceramic by pyrolysis to render the substrate and the feature(s) PDCs so that the features become a DR, such as DR 510 described above. The device can then be coated with photoresist and patterned. High-temperature metals, such as Pt and Pd, can then be coated to form the antenna and microstrip line, which as described above are used to couple RF energy into the DR. The photoresist can then be removed.

Embodiments of the invention provide several significant advantages over conventional sensing systems for sensing pressure or temperature. One advantage is provided by the wireless aspect, specifically being based on a wireless resonant frequency sensing technique. The reader unit, which generally includes a processor having an associate memory with stored calibration data, can read out the temperature/pressure or other parameter information sensed by the passive PDC sensors without the need for wire connections. Therefore, the sensors can be used to measure the temperature/pressure at almost any location inside challenging sensing locations, such as in an engine chamber, including around the rotating engine blades. Resonators having high-Q factor (>3,000 at 20 GHz) have been developed by the Inventors using MEMS. Such resonator structures can also be used for sensing applications. The high-Q factor PDC MEMS resonator structures enable the use of wireless sensing techniques for high-temperature (>1000° C.) applications.

Another advantage of disclosed embodiments relates to the passive nature of the sensors. Disclosed temperature/pressure sensors do not contain any active device or component since the wireless sensing technique disclosed herein is passive. Only PDC materials and stable metals are used. In addition, as described above, metals can be covered by a high-temperature dielectric coating material to prevent oxidization. As a result, sensors according to embodiments of the invention can be robust even in harsh environments.

High accuracy provided by disclosed embodiments is another advantage. The resonant frequency of the evanescent-mode resonator structures disclosed herein has been shown to be very sensitive to the pressure. Also, the dielectric constant of PDCs has been demonstrated to be strongly temperature-dependent. As described above, wireless sensing techniques based on high-Q factor resonators are able to detect a slight change in the resonant frequency of the sensors, where using stored calibration data the sensed resonant frequency can be converted to a specific temperature or pressure values.

Robustness is another advantage provided by disclosed embodiments. The highly oxidation/corrosion resistant nature of the PDCs makes the sensors robust in extremely harsh environments. Since the RF reader units can be remotely placed in a location that provides a conventional temperature (near room temperature), the potential adverse effects from the high temperature being sensed can be eliminated.

Other advantages provided by disclosed embodiments include small size and flexibility. The size of the passive PDC sensors can be very small depending on the working frequency. Thus, "spot" temperature/pressure sensing becomes possible. Low cost is also generally provided by disclosed embodiments. The cost for fabricating the passive PDC sensors is low due to the small quantities of materials required and the simple and high volume capable processing techniques, such as MEMS. Due to the continued development of RF/microwave circuit technology, the cost of the reader unit is generally modest and will likely continue to decrease in cost.

Embodiments of the invention can be widely used in a variety of systems. Exemplary systems include, but are not limited to, high-temperature systems such as turbine engines, turbine generators, nuclear power plants, and rockets, among others.

While various embodiments of the invention have been described above, it should be understood that they have been presented by way of example only, and not limitation. Numerous changes to the disclosed embodiments can be made in accordance with the disclosure herein without departing from the spirit or scope of this Disclosure. Thus, the breadth and scope of this Disclosure should not be limited by any of the above described embodiments. Rather, the scope of this Disclosure should be defined in accordance with the following claims and their equivalents.

Although embodiments of the invention has been illustrated and described with respect to one or more implementations, equivalent alterations and modifications will occur to others skilled in the art upon the reading and understanding of this specification and the annexed drawings. In particular regard to the various functions performed by the above described components (assemblies, devices, circuits, systems, etc.), the terms (including a reference to a "means") used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the invention. In addition, while a particular feature of the invention may have been disclosed with respect to only one of several implementations, such feature may be combined with one or more other features of the other implementations as may be desired and advantageous for any given or particular application. Furthermore, to the extent that the terms "including," "includes," "having," "has," "with," or variants thereof are used in either the detailed description and/or the claims, such terms are intended to be inclusive in a manner similar to the term "comprising."

We claim:

1. A RF resonator for sensing a physical or an environmental parameter, comprising:
    a substrate having a substrate surface, and
    a polymer-derived ceramic (PDC) element positioned on or within said substrate surface, wherein said RF resonator has a resonant frequency that changes as a function of said physical or said environmental parameter.

2. The RF resonator of claim 1, wherein a quality (Q) factor of said RF resonator is ≥100.

3. The RF resonator of claim 1, wherein a nominal resonant frequency of said RF resonator is between 1 and 40 GHz.

4. The RF resonator of claim 1, further comprising a coupling structure including a planar antenna on or above said substrate surface for coupling RF energy to and from said RF resonator.

5. The RF resonator of claim 4, wherein said RF resonator comprises an evanescent-mode pressure sensitive resonator, and said substrate having said substrate surface further comprises a cavity formed in said substrate, and said RF resonator further comprises a flexible top plate on said cavity, and said PDC element comprises at least one metal coated PDC post within said cavity, said evanescent-mode resonator having a pressure sensitive resonant frequency that changes as a gap between said PDC post and said top plate changes,
    and said coupling structure further comprises a slot formed in said flexible top plate.

6. The RF resonator of claim 1, wherein said RF resonator comprises an evanescent-mode pressure sensitive resonator, and said substrate having said substrate surface further comprises a cavity formed in said substrate, said RF resonator further comprises a flexible top plate on said cavity, and said PDC element comprises at least one metal coated PDC post within said cavity, said evanescent-mode resonator having a pressure sensitive resonant frequency that changes as a gap between said PDC post and said top plate changes.

7. The RF resonator of claim 6, wherein said PDC element includes a metal coating and a dielectric coating on said metal coating that prevents oxidation of said metal.

8. The RF resonator of claim 1, wherein said RF resonator comprises a temperature sensitive resonator and said PDC element comprises a dielectric resonator (DR) that has a temperature sensitive dielectric constant on said substrate surface.

9. The RF resonator of claim 8, wherein said substrate comprises a ceramic substrate.

10. The RF resonator of claim 1, wherein said PDC element comprises SiAlCN, SiCN or SiBCN.

11. A system for wirelessly sensing at least one physical or environmental parameter, comprising:
    at least one RF resonator for sensing said physical or said environmental parameter comprising:
        a substrate having a substrate surface, and
        a polymer-derived ceramic (PDC) element positioned on or within said substrate surface, wherein said RF resonator has a resonant frequency that changes as a function of said physical or said environmental parameter, and
    a wireless RF reader located remotely from said RF resonator, said wireless RF reader for transmitting a wideband RF interrogation signal that excites said RF resonator, wherein said wireless RF reader detects a sensing signal retransmitted by said RF resonator and includes a processor for determining said physical or environmental parameter at a location of said RF resonator.

12. The system of claim 11, wherein a nominal resonant frequency of said RF resonator is between 1 and 40 GHz.

13. The system of claim 11, further comprising a coupling structure including a planar antenna on or above said substrate surface for coupling RF energy to and from said RF resonator.

14. The system of claim 11, wherein said RF resonator comprises an evanescent-mode pressure sensitive resonator, and said substrate having said substrate surface further comprises a cavity formed in said substrate, said RF resonator further comprises a flexible top plate on said cavity, and said PDC element comprising at least one metal coated PDC post within said cavity, said evanescent-mode resonator having a pressure sensitive resonant frequency that changes as a gap between said PDC post and said top plate changes.

15. The system of claim 14, wherein said PDC element includes a metal coating and a dielectric coating on said metal coating that prevents oxidation of said metal.

16. The system of claim 11, wherein said RF resonator comprises an evanescent-mode pressure sensitive resonator, and said substrate having said substrate surface further comprises a cavity formed in said substrate, and said RF resonator further comprises a flexible top plate on said cavity, and said PDC element comprises at least one metal coated PDC post within said cavity, said evanescent-mode resonator having a pressure sensitive resonant frequency that changes as a gap between said PDC post and said top plate changes,
    and said coupling structure further comprises a slot formed in said flexible top plate.

17. The system of claim 11, wherein said RF resonator comprises a temperature sensitive resonator and said PDC element comprises a dielectric resonator (DR) that has a temperature sensitive dielectric constant on said substrate surface.

18. The system of claim 11, wherein said PDC element comprises SiAlCN, SiCN or SiBCN.

19. The system of claim 11, wherein said at least one RF resonator comprises a plurality of said RF resonators, said plurality of said RF resonators bonded to different locations within said system.

20. The system of claim 19, wherein said plurality of said RF resonators each provide different resonant frequencies.

21. The system of claim 11, wherein said system comprises a turbine engine comprising a turbine blade, and wherein said RF resonator is bonded to said turbine blade.

22. A method of forming an RF resonator for sensing a physical or an environmental parameter, comprising:
    providing a substrate comprising a substrate surface having a polymer-derived ceramic (PDC) precursor within or thereon;
    lithographically defining at least one element comprising said PDC precursor, and
    converting said element into a PDC element, wherein said RF resonator has a resonant frequency that changes as a function of said physical or said environmental parameter.

23. The method of claim 22, wherein said converting comprises pyrolysis.

24. The method of claim 22, further comprising the step of modifying said PDC precursor by adding monomers comprising vinyl groups before said lithographically forming.

25. The method of claim 22, wherein said RF resonator comprises an evanescent-mode pressure sensitive resonator, and said lithographically forming further comprises forming a cavity in said substrate, wherein said PDC element is within said cavity, further comprising:
  forming a flexible top plate;
  bonding said flexible top plate onto said cavity.

26. The method of claim 22, wherein said RF resonator comprises a temperature sensitive resonator and said PDC element comprises a dielectric resonator (DR) that has a temperature sensitive dielectric constant on said substrate surface.

27. The method of claim 22, wherein said PDC element comprises SiAlCN, SiCN or SiBCN.

\* \* \* \* \*